United States Patent [19]

Kimura et al.

[11] Patent Number: 4,793,358
[45] Date of Patent: Dec. 27, 1988

[54] APPARATUS FOR MEASURING LOCAL CEREBRAL BLOOD FLOW

[75] Inventors: Tokunori Kimura, Utsunomiya; Naotoshi Kobayashi, Kawasaki, both of Japan

[73] Assignee: Kabushiki Kaisha Toshiba, Kawasaki, Japan

[21] Appl. No.: 17,047

[22] Filed: Feb. 20, 1987

[30] Foreign Application Priority Data

Feb. 25, 1986 [JP] Japan .................................. 61-40044

[51] Int. Cl.$^4$ ............................................. A61B 6/00
[52] U.S. Cl. .................................... 128/654; 128/719; 250/303
[58] Field of Search ............... 128/653, 654, 719, 730; 250/380, 303

[56] References Cited

U.S. PATENT DOCUMENTS

| | | | |
|---|---|---|---|
| 3,769,966 | 11/1973 | Youdin et al. | 128/654 |
| 3,976,050 | 8/1976 | Glasser et al. | 128/654 |
| 4,233,842 | 11/1980 | Raemer et al. | 128/719 |
| 4,535,780 | 8/1985 | Gur et al. | 128/659 |

FOREIGN PATENT DOCUMENTS 2418786 10/1974 Fed. Rep. of Germany ...... 128/654
0147229 11/1980 Japan .................................. 128/654

OTHER PUBLICATIONS

Seylaz et al., "Analytical Problems Associated with the Noninvasive Measurements of Cerebral Blood Flow in Cerebrovascular Diseases" Med & Biol Eng & Comput 1980 pp. 39–47.

Anderson et al., "An Automated Cerebral Blood Flow Analyzer: Concise Communication", Journal of Nuclear Medicine, vol. 18, No. 7, Jul. 1977, pp. 728–731.

Primary Examiner—Ruth S. Smith
Attorney, Agent, or Firm—Finnegan, Henderson, Farabow, Garrett, & Dunner

[57] ABSTRACT

A local cerebral blood flow measuring apparatus includes an expiratory tube arranged along a slice within a photography area of a gantry, and a sensor for detecting end of expiration. The expiratory tube includes a chamber for storing only an end tidal air, in synchronism with the end of expiration detected by the sensor. The end tidal air storage chamber and a subject to be examined are scanned with X-rays from the gantry, in synchronism with the end tidal air. The tracer concentration of the end tidal air storage chamber is measured by means of data derived from the gantry.

9 Claims, 6 Drawing Sheets

F I G. 1
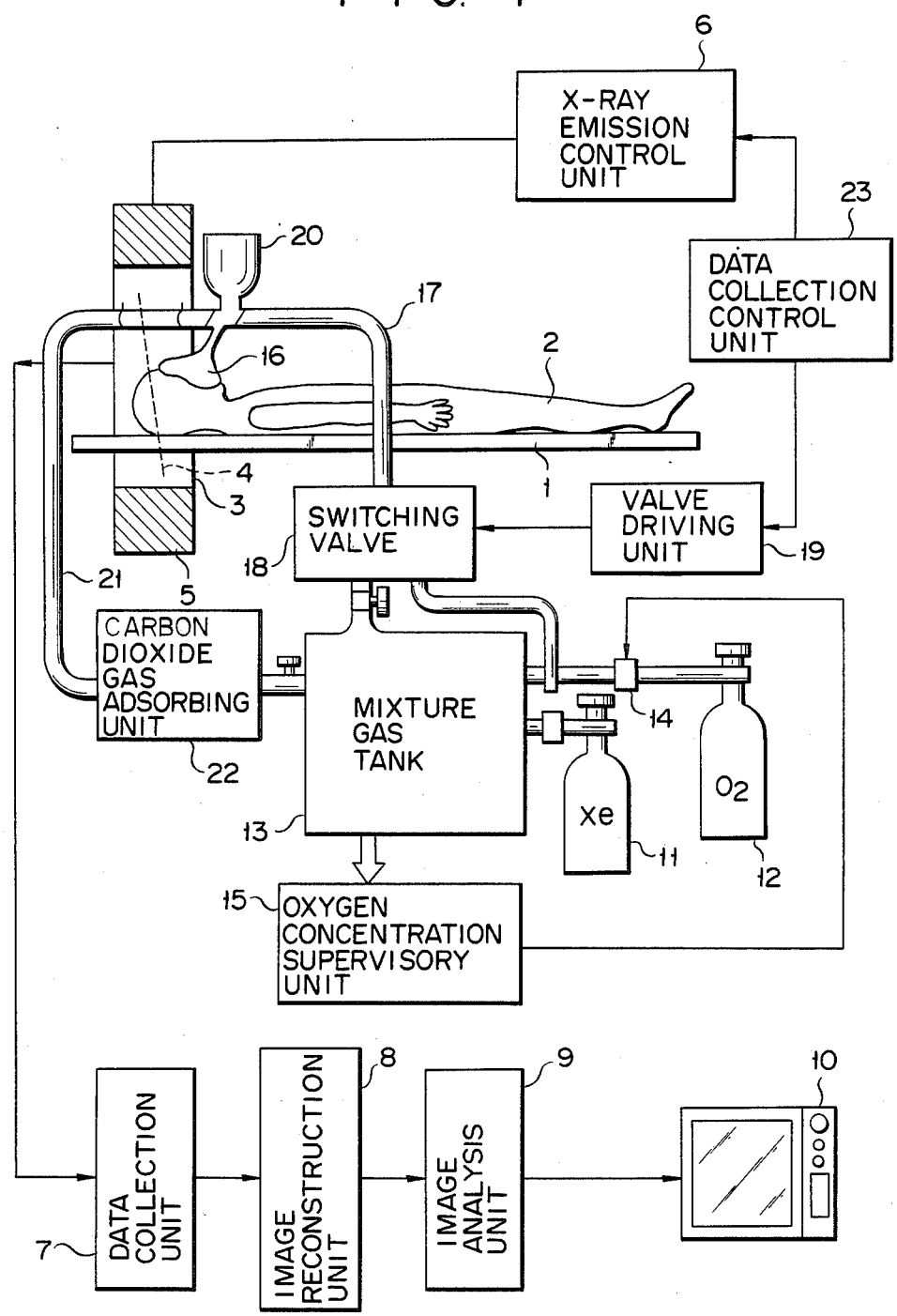

APPARATUS FOR MEASURING LOCAL CEREBRAL BLOOD FLOW

BACKGROUND OF THE INVENTION

The present invention relates to an apparatus for measuring local cerebral blood flow.

Conventional apparatuses for measuring local cerebral blood flow include a single photon emission CT (SPECT) and a positron emission CT (PET). These apparatuses can measure r-CBF values. Among the conventional CT apparatuses, a CT apparatus for measuring local cerebral blood flow according to a tracer inhalation method has received a great deal of attention, since it has significant advantages as regards spatial resolution, quantum and cost performance when the local cerebral blood flow is reproduced as a functional image.

According to the tracer inhalation method, the concentration of a tracer in arterial blood and a time-concentration curve relative to the tracer concentration in the cerebral tissue are obtained by means of dynamic scanning using an X-ray CT apparatus while a nondiffusable gas such as Xe (Xenon) is inhaled as a tracer into the lungs. A distribution coefficient $\lambda$ between the blood and the cerebral tissue and the blood flow rate are calculated in each matrix of a slice, according to the Kety-Schmidt's formula, using the measured data. The calculated result is displayed as a functional image.

Tracer concentration Ca(t) in the arterial blood is calculated on the basis of a principle (Henley law) wherein a given concentration of tracer in the arterial blood has an equilibrium relationship with that in the alveolar air flowing from the alveoli of the lungs. Tracer concentration Ce(T) in the end tidal air, which corresponds to the alveolar air, is calculated to obtain the concentration Ca(t) present in the arterial blood.

U.S. patent application No. 746,523 now abandoned describes an apparatus using the above method. In this apparatus, exhaled air in cavities such as the windpipe, the nasal cavity, or the inner cavity of a breathing mask is exhausted into an expiratory tube. If the subject inhales air which includes a tracer, the rate of rise in the concentration of tracer in the expiratory tube increases. However, if the subject inhales only air or pure oxygen, the rate of fall in the concentration of tracer in the expiratory tube increases. An X-ray CT scan normally requires a period of 4 to 9 seconds. The tracer concentration is measured as an average of the number of breathing cycles which occur during the time of scanning a scan plane in the expiratory tube. Therefore, the rate of rise and fall in tracer concentration are further increased. For this reason, the changes with time (i.e., the increase add decrease) in the tracer concentration, measured by scanning the expiratory tube, are greater than those which occur in the actual end tidal air (i.e., the tail-end of the exhalation, from the end of the current exhalation cycle to the beginning of the next inhalation cycle. The end tidal air seems to correspond to the alveolar air). As a result, the cerebral blood flow cannot be accurately measured.

SUMMARY OF THE INVENTION

It is an object of the present invention to provide a CT apparatus for measuring cerebral blood flow wherein the concentration of a tracer in the end tidal air, as well as the cerebral blood flow, can be measured with a high degree of precision.

According to the present invention, an expiratory tube is located within a tomography area, so as to cross a slice of a subject to be examined. Exhaled air containing a tracer passes through the expiratory tube, and that part of the expiratory tube corresponding to the slice is scanned to measure the tracer concentration, in synchronism with breathing, whereby an accurate measurement of the tracer concentration can be obtained.

BRIEF EXPLANATION OF THE DRAWINGS

FIG. 1 is a block diagram of a CT apparatus for measuring local cerebral blood flow according to an embodiment of the present invention;

DETAILED DESCRIPTION OF THE PREFERRED EMBODIMENTS

Figure 2:
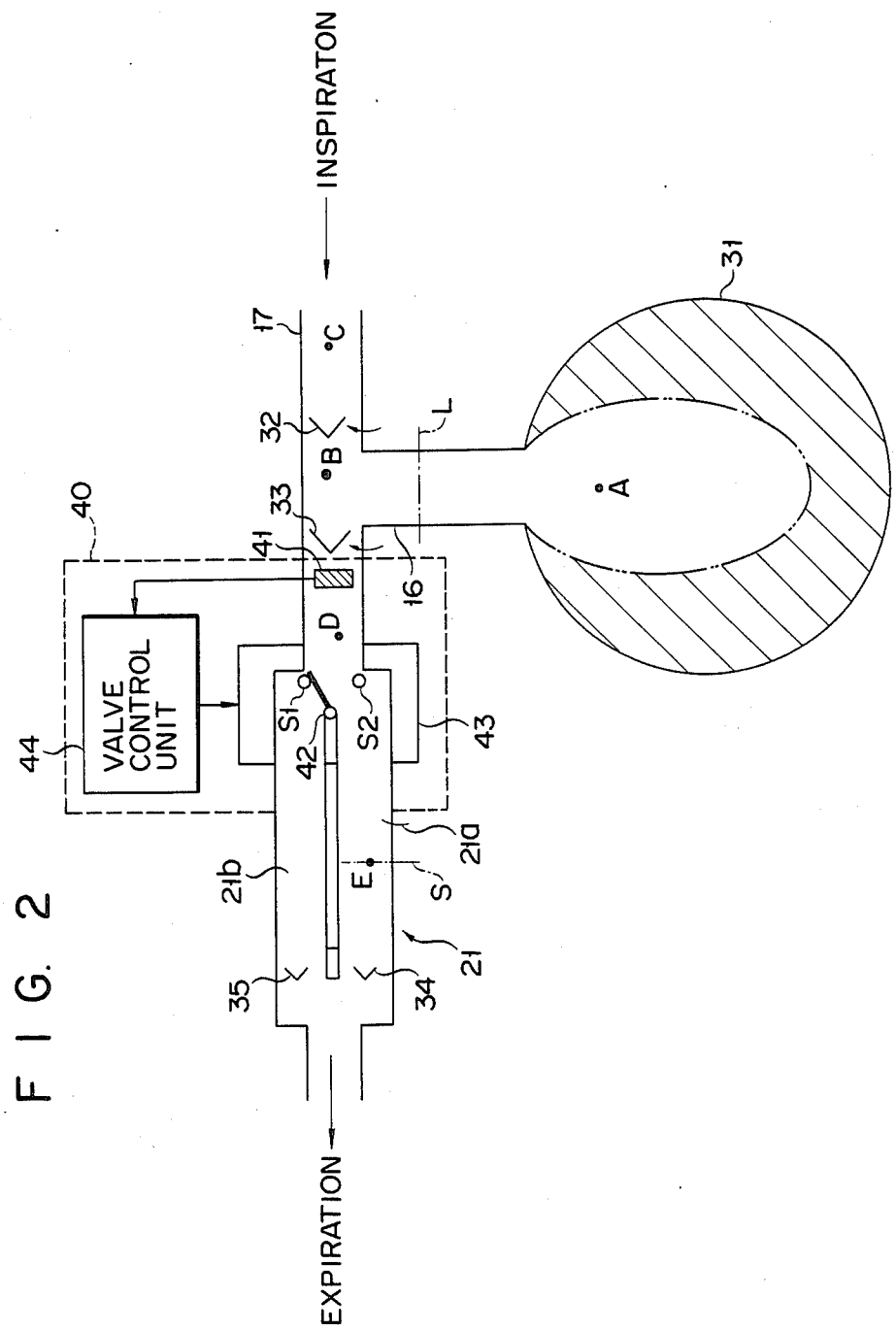
FIG. 2 is a schematic view of a tracer concentration measuring section.

FIG. 1 shows gantry 5 having photography hole 3. The head of a subject to be examined, i.e., patient 2 lying on bed 1, is inserted in hole 3. Gantry 5 can be rotated around the head of patient 2. An X-ray tube emits X-rays along slice 4. X-ray emission control unit 6 is connected to gantry 5, and controls the supply of high voltage to the X-ray tube, thereby controlling X-ray exposure. An output from an X-ray sensor (not shown) arranged in gantry 5 is connected to data collection unit 7. Unit 7 acquires projection data sent from gantry 5, and sends projection data to image reconstruction unit 8. Unit 8 reconstructs a tomogram along slice 4 according to a known method using projection data supplied by data collection unit 7. An output from reconstruction unit 8 is transmitted to image analysis unit 9. Unit 9 analyzes tracer concentration Ca(t) in the arterial blood and tracer concentration Ci in the cerebral tissue on the basis of image data representing a plurality of time-serial tomograms supplied by image reconstruction unit 8. An output from analysis unit 9 is transmitted to image display unit 10. Unit 10 displays tomograms reconstructed by reconstruction unit 8, numeric data $\lambda i$ (position coefficient), ki (build up rate), and fi (blood flow rate) obtained by analysis of unit 9, and a functional image corresponding to the observed portions of the patient, e.g., various curves indicating measured values of the data.

The tracer inspiratory section is a closed system. This enables the tracer to be reused. Tracer cylinder 11 for storing a tracer, for example, Xe gas, and oxygen cylinder 12 of storing oxygen are coupled to mixture gas tank 13. Tank 13 is coupled to oxygen concentration supervisory unit 15 for monitoring the concentration of oxygen mixed with the tracer therein, and for automatically controlling control valve 14. Valve 14 controls the flow rate of oxygen so as to maintain the oxygen concentration at a predetermined value.

Mask 16 for covering the nose of patient 2 is coupled to switching valve 18 by means of inspiratory tube 17. A check valve (not shown) is arranged in inspiratory tube 17, near mask 16, to supply the mixture gas to mask 16 and to prevent the exhaled air from becoming mixed with the inspiratory air. Valve 18 is coupled to mixture gas tank 13 and oxygen cylinder 12, to switch from the mixture gas to oxygen or vice versa. Valve 18 is connected to and driven by valve-driving unit 19. Buffer envelope 20 is coupled to mask 16 and inspiratory tube 17, so as to moderate the pressure of the mixture gas supplied through tube 17.

Expiratory tube 21 is coupled to mask 16 and mixture gas tank 13 via carbon dioxide gas-adsorbing unit 22. It should be noted that tube 21 is arranged to extend through slice 4. Adsorbing unit 22 adsorbs and removes carbon dioxide gas.

Data collection control unit 23 controls X-ray emission timing by means of X-ray emission control unit 6, as well as switching timing for the mixture gas and oxygen by means of valve-driving unit 19.

FIG. 2 shows the main part of the tracer intake section. Expiratory tube 21, extending through slice 4, branches off into first expiratory path 21a through which only the end tidal air from the lungs 31 of the patient 2 passes, and second expiratory path 21b through which gas excluding the end tidal air passes. Check valves 34 and 35 are arranged near the outlet ports of paths 21a and 21b, so that the gas exhausted from one path does not flow into the other path.

Path selection unit 40 is arranged near the inlet ports of paths 21a and 21b, to selectively change the flow path. Path selection unit 40 comprises flow sensor 41 arranged in an expiratory tube portion where tube 21 does not branch off into first and second paths 21a and 21b, and also comprises valve 42 arranged in the branching point of first and second paths 21a and 21b. Valve 42 is driven by valve driver 43. Driver 43 is controlled by valve control unit 44 in response to an output signal from flow sensor 41. Flow sensor 41 is arranged to detect the flow rate or the speed o the air being breathed, in particular, the air being expired.

Figure 3:
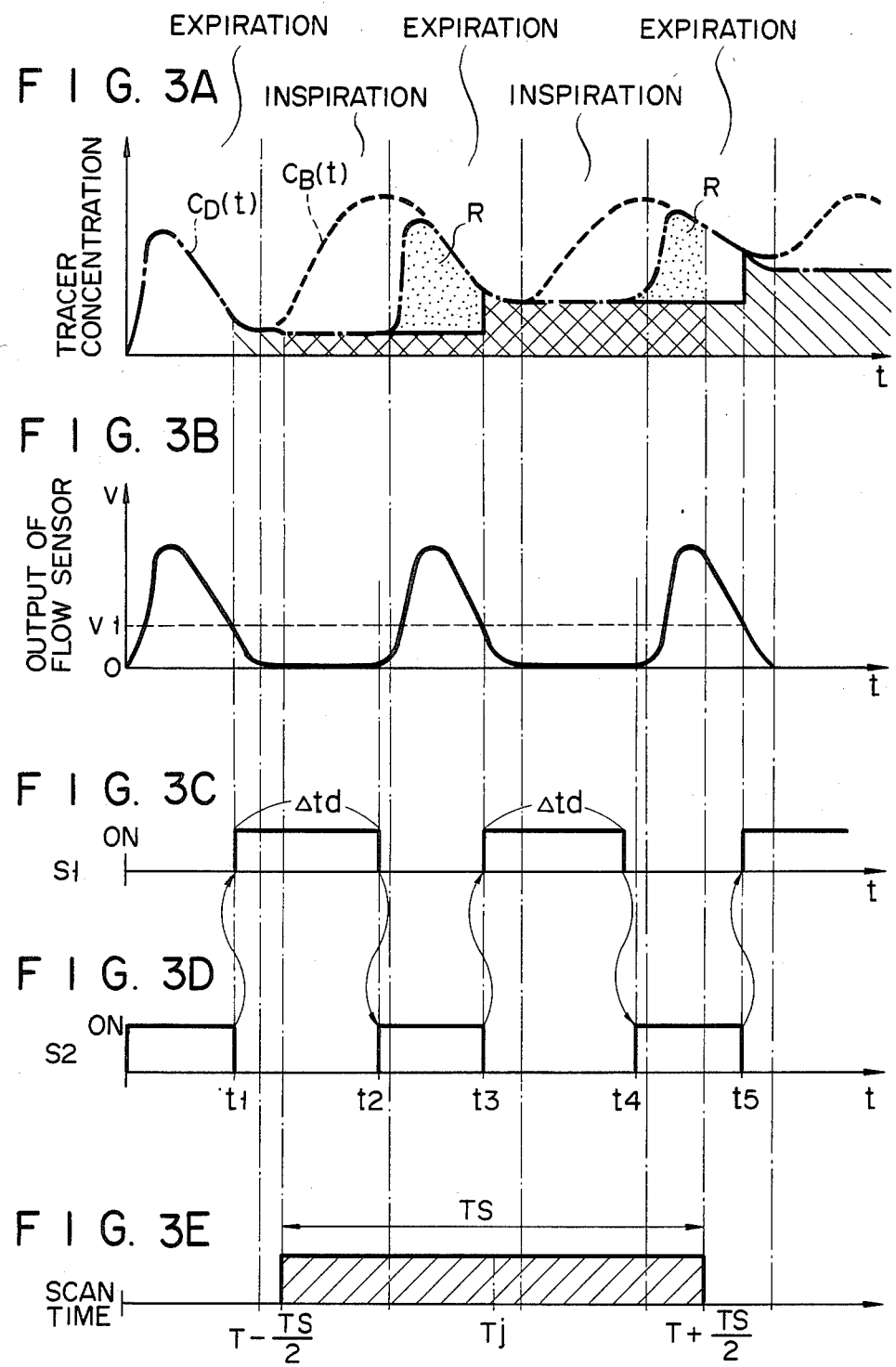
FIGS. 3A to 3E are timing charts showing switching timings of a valve shown in FIG. 2.

An operation for measuring local cerebral blood flow will now be described, with reference to timing charts of FIGS. 3A to 3E. FIG. 3A shows tracer concentration $C_D(t)$ at point D shown in FIG. 2, and tracer concentration $C_B(t)$ at point B therein. FIG. 3B shows a reading of exhalation flow-speed obtained from flow sensor 41. Valve control unit 44 receives the output signal from flow sensor 41, compares threshold level v1 shown in FIG. 3B with the output signal from flow sensor 41, and drives valve 42 in accordance with the timing shown in FIGS. 3C and 3D. More specifically, when output signal v (FIG. 3B) from flow sensor 41 satisfies inequality $v < v1$, valve 42 is switched to S1.

Threshold level v1 is set at the level of the output signal obtained from flow sensor 41 when the exhaled gas inserted into path 21a after valve 42 is switched from S2 to S1 reaches point E of scan plane S. Valve control unit 44 controls valve driver 43 to cause it to switch valve 42 from S1 to S2 when delay time $\Delta td$ has elapsed after valve 42 is switched from S2 to S1, as is shown in FIGS. 3C and 3D. Valve 42 is switched from S1 to S2 while expiration check valve 33 is closed during the inspiration cycle. Time $\Delta td$ begins at the end of the expiration cycle (t1 in FIG. 3C) when the output of the flow sensor 41 is at threshold value v1 and ends at a preselected time after the valve is switched from S2 to S1 corresponding to the start of the expiration cycle and the opening of check valve 33. In the course of valve 42 being switched back and forth as described above, the concentration of the exhaled gas supplied to first expiratory path 21a changes, as indicated by cross-hatched lines in FIG. 3A. The exhaled gas is guided to first path 21a until delay time $\Delta td$ has elapsed after expiration speed v drops to lower than threshold level v1. Thus, only the end tidal air is supplied to first path 21a, the other expiratory components being guided to second path 21b.

An X-ray CT scan is performed, for one scan period Ts having central scan time Tj, at point E in first expiration path 21a. As is shown in FIG. 3E, scanning is performed for a period from time $(Tj - Ts/2)$ to time $(Tj + Ts/2)$. As a result, the expiration which is the subject of the CT scan is defined by the cross-hatched portion in FIG. 3A. A CT value in first expiratory path 21a can be calculated as an average value of an integral from time $(Tj - Ts/2)$ to time $(Tj + Ts/2)$ of $Ce(t)$ as follows:

$$(1/Ts) \int_{Tj - Ts/2}^{Tj + Ts/2} Ce(t) dt$$

As is apparent from the current CT apparatus, one scanning period takes place during several breathing cycles (two or three cycles), and the resultant CT value obtained is an average value as a function of time. In view of this averaging, the precision of the resultant $Ce(t)$ value as measured by the CT apparatus at point E is not significantly affected since the error is small compared to the value of $Ce(t)$. Even if a CT value is obtained by one scanning during a period of one second, the CT value obtained has essentially no affect on the value of $Ce(t)$.

Figure 4:
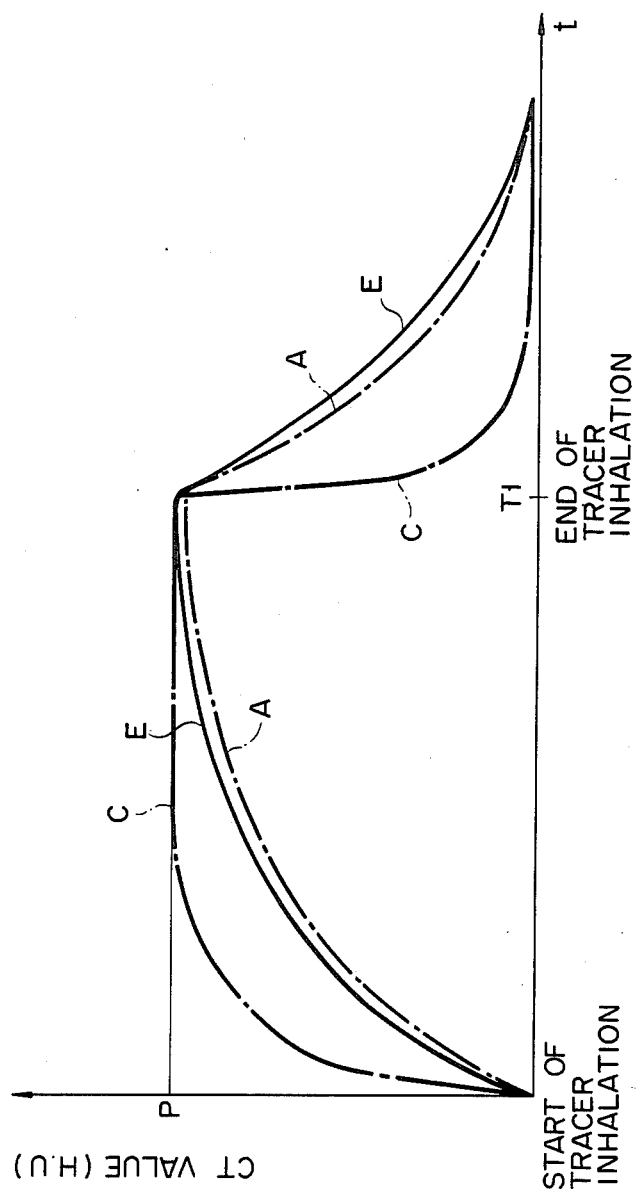
FIG. 4 is a graph showing the tracer concentration as a function of time.

FIG. 4 shows changes in tracer concentration as a function of time at points A, C and E. The tracer concentration at point E within first expiration path 21a is very close to that in the actual end tidal air, i.e., the tracer concentration at point A. Thus, the measuring precision can be greatly improved as compared with the conventional case.

Tracer concentration $Ca(t)$ in the arterial blood is calculated by image analysis unit 9 on the basis of tracer concentration $Ce(t)$ in the end tidal air. This calculation operation will be described below.

The time-concentration curve obtained by performing scanning at point E is used as discrete data, and is represented as $C_E(tj)$ (for $j = 1, 2, \ldots n$). Data $C_E(tj)$ can be used as tracer concentration data of the end tidal air. However, if a tracer is inhaled in a constant concentration and if the time period is constant for each inhalation, any increase and decrease in the tracer concentration in the arterial blood can be expressed or approximated by primary exponential functions. Tracer concentrations represented by the primary exponential functions are subjected to time-curve fitting by a method of least squares and can be converted into continuous functions. In other words, the plots are converted into values constituting a continuous curve.

Tracer concentration $Ca(t)$ in the arterial blood can be calculated using reduction coefficient $\alpha t$:

$$Ca(t) = \alpha t \times C_E(tj)$$

for $\alpha t \approx 0.0011 \times Ht + 0.10$ (where Ht is a hematocrit value (%) of blood.

$C_E(t)$ corresponds to the value obtained by the following equation:

$$C_e(t) = \begin{cases} P(1 - e^{-at}) & \text{for } 0 < t \leq T1 \\ P(1 - e^{-aT1})e^{-a(t-T1)} & \text{for } t > T1 \end{cases}$$

where P is the peak value of tracer concentration, shown in FIG. 4, a tracer of a constant concentration being inhaled during a period T1, and a represents the rate of rise of Ce(t).

Rate-of-rise figure a increases quite rapidly in conventional apparatus; however, a more accurate rate-of-rise figure a can be obtained in the apparatus of the present invention, whereby the accuracy of value Ca(t) is significantly improved.

To further improve the measuring precision, a correction value for rate-of-rise figure a is given as Δa, and Ce(t) can be reduced by use of the following equation:

$$Ca(t) = \begin{cases} at\,P1 - e^{-(a+\Delta a)t} & \text{for } 0 < t \leq T1 \\ at\,P1 - e^{-(a+\Delta a)T1} e^{-(a+a)(t-T1)} & \text{for } t > T1 \end{cases}$$

Correction value Δa is known to be less than 0, according to previous tests. The actual correction value depends on threshold level vl1, and must be experimentally measured.

Figure 5:
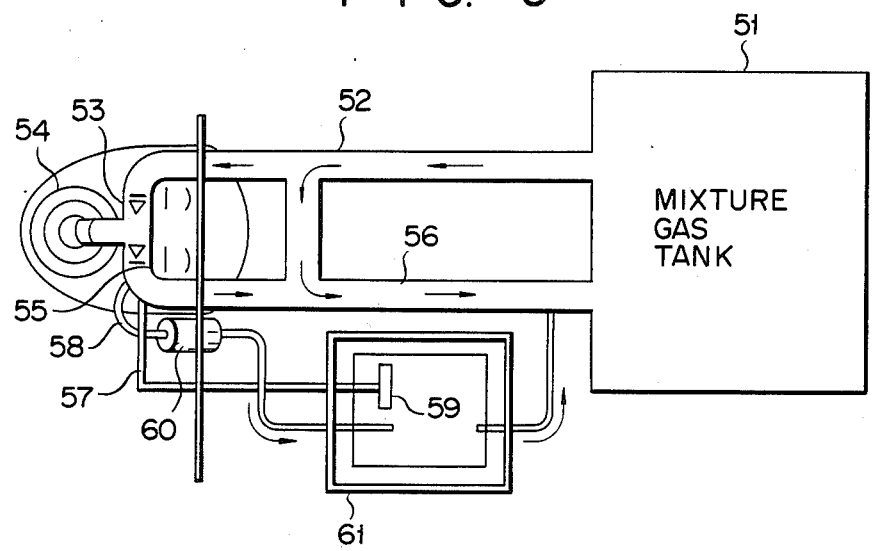
FIG. 5 is a schematic plan view of a tracer concentration measuring section in a CT apparatus according to another embodiment of the present invention.
Figure 6:
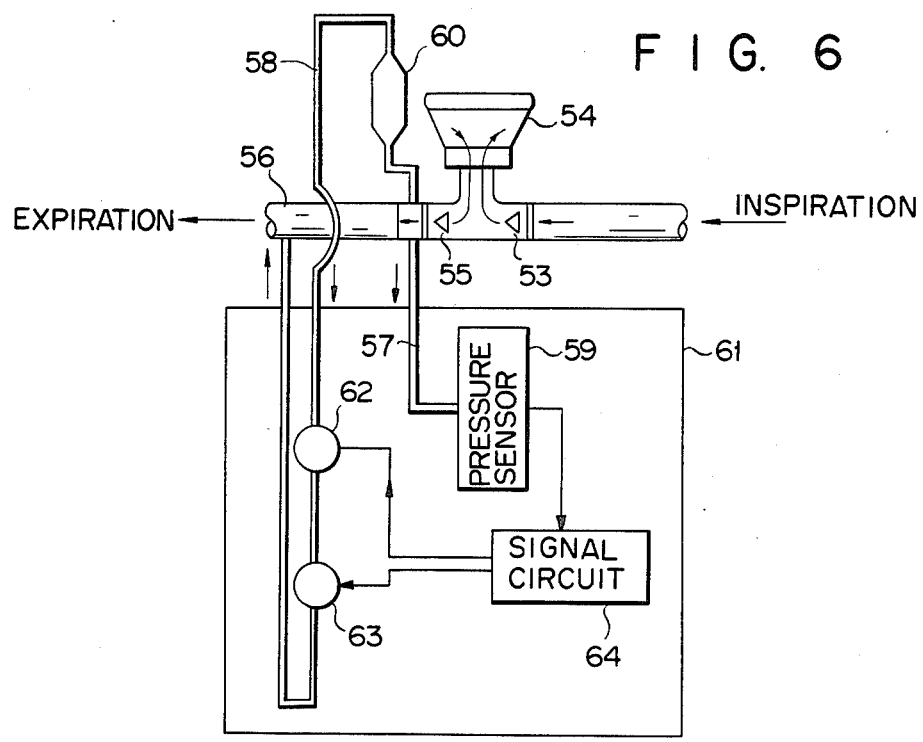
FIG. 6 is a schematic side view of a tracer concentration measuring section in the CT apparatus shown in FIG. 5; and FIG: 7 is a timing chart showing the operation of the CT apparatus shown in FIGS. 5 and 6.

Another embodiment of the present invention will now be described with reference to FIGS. 5 and 6. According to this embodiment inspiratory tube 52, coupled to mixture gas tank 51, is coupled to mask 54 via inspiratory check valve 53. Mask 54 is coupled to expiratory tube 56 via expiration check valve 55. Pressure transmission tube 57 and end tidal air sampling tube 58 are connected to the outlet port of valve 55. The distal end of tube 57 is coupled to pressure sensor 59. Tube 58 is coupled to end tidal air sampling device 61 via tracer concentration measuring chamber 60.

In end tidal air-sampling device 61, the outlet port of tracer concentration measuring chamber 60 is sequentially connected to sampling pump 62 and electromagnetic valve 63. The outlet port of valve 63 is coupled to expiratory tube 56.

The output terminal of pressure sensor 59 is connected to signal circuit 64. The output terminal of signal circuit 64 is connected to sampling pump 62 and electromagnetic valve 63.

Figure 7:
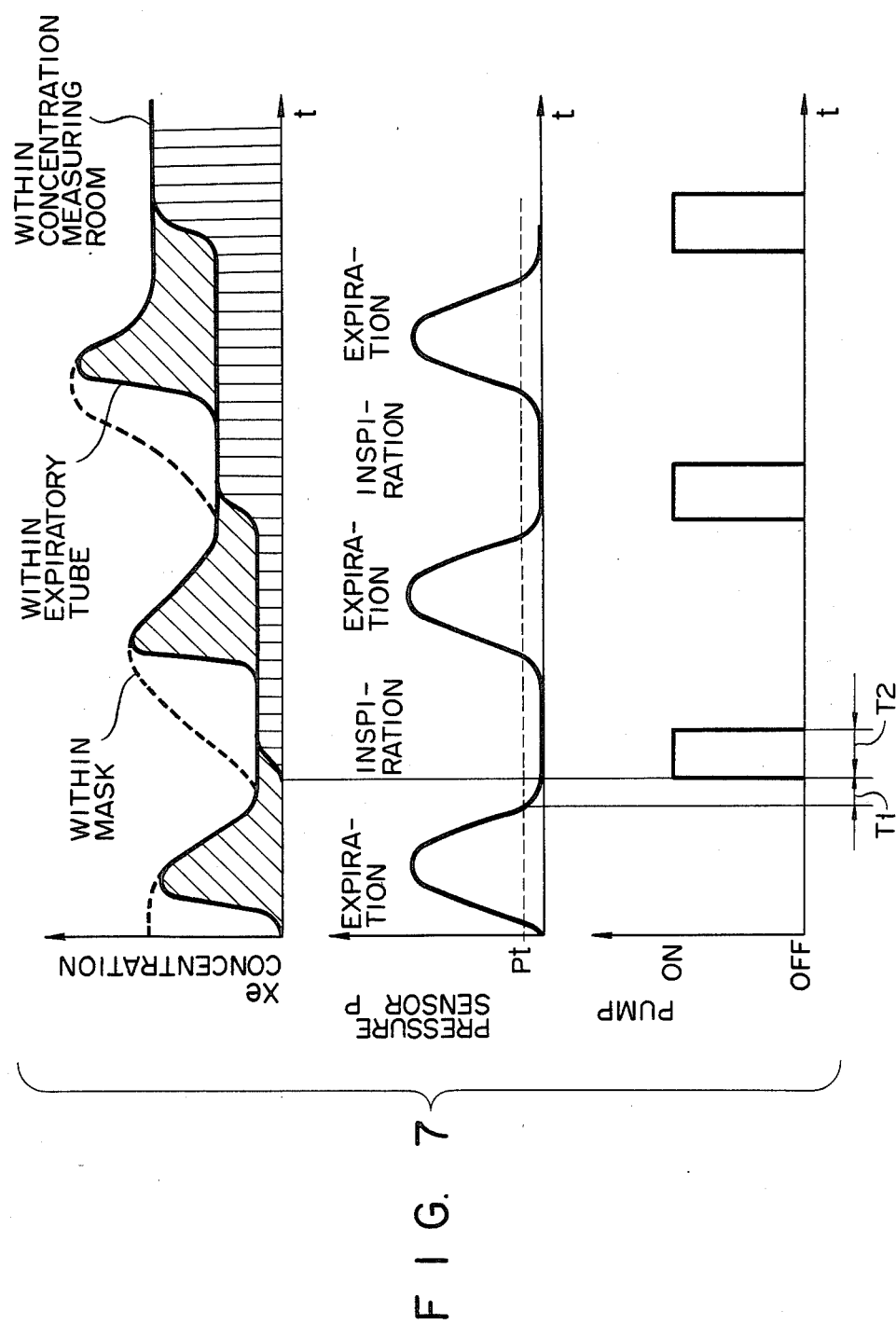

With the above apparatus, a mixture gas including a tracer gas (Xenon gas) and oxygen is supplied from mixture gas tank 51, and is received by mask 54, having passed through inspiratory tube 52 and inspiratory valve 53. The gas exhaled by the patient in the normal course of breathing is exhausted into expiratory tube 56, after passing through expiratory valve 55. The exhaled gas contained in expiratory tube 56 is supplied to pressure sensor 59 and tracer concentration measuring chamber 60, via end tidal air sampling tube 58. Sensor 59 detects the pressure of the exhaled gas and outputs a detection signal, as shown in FIG. 7. The pressure of the exhaled gas gradually increases from the beginning of expiration and then gradually decreases toward the end of expiration.

The expiratory pressure signal is input to signal circuit 64 where it is compared with a threshold level, and the end tidal air is detected during time period T1. Signal circuit 64 sends a drive signal to sampling pump 62 and electromagnetic valve 63 when a predetermined period of time (T1=about one second) has elapsed after the detection of the end tidal air. Sampling pump 62 is driven and electromagnetic valve 63 is opened. In this case, the end tidal air flows into tracer concentration measuring chamber 60. The drive signal is disabled when a predetermined period of time T2 has elapsed, whereupon sampling pump 62 and electromagnetic valve 63 are deenergized.

The above operation is repeated to supply only the end tidal air to tracer concentration measuring chamber 60. Chamber 60 is located on slice 4 in photography hole 3 of gantry 5, and is scanned with X-rays to measure the tracer concentration therein.

As is apparent from the above description, the expiratory pressure can be detected by pressure sensor 59, as the expiratory gas through pressure transmission tube 57. The expiratory gas encounters no resistance as it passes through the expiratory path, and even a low expiratory pressure can be accurately detected. In addition, expiratory pressure measurement is free from such adverse influences as dust, humidity, and the like. In addition, the detection sensitivity of the pressure sensor can be adjusted to ensure an optimal level.

The period from the reception timing of the expiratory signal to the sampling-start timing can be arbitrarily determined to prevent the gas excluding the end tidal air gas from being sampled in the event that irregular breathing occurs. If at least two expiratory cycles occur in rapid succession, for instance, due to the subject sneezing, an end tidal air signal is output at the end of the first expiratory cycle. In this case, the gas located at the sampling position is not the end tidal air, and therefore should not be sampled. Accordingly, a predetermined delay time is set after the detection of the end tidal air. If the second expiratory cycle begins during the waiting time and is detected, the delay time is reset. As a result, the gas excluding the end tidal air is not sampled.

When the next expiratory cycle commences during sampling, the sampling seep is interrupted. Since the sampling time is variable, it can be adjusted according to the number of samples.

A sampling circuit system comprises a pump and an electromagnetic value. The pump and the electromagnetic value are simultaneously energized at the beginning and end of sampling. Unnecessary gas sampling caused by residual pressure and inertia of the gas in the sampling circuit system after deenergization of the pump does not occur, and only the end tidal air is detected.

The end tidal air can be detected in synchronism with the patient exhaling; thus, only the end tidal air is detected. In this way, the tracer concentration can be accurately measured. It should be noted that sampling may alternatively be performed in synchronism with inspiration instead of expiration.

What is claimed is:

1. An apparatus for measuring local cerebral blood flow of a patient under examination, said apparatus comprising:
   gantry means for supporting the patient during examination, said gentry means including a photography area in which a portion of the patient to be examined is positioned and means for scanning said portion of the patient with X-rays along a slice of said portion of the patient to produce tomographic image data indicative of cerebral blood flow in the patient;

inspiratory gas means for supplying a tracer gas to the patient during an inspiration cycle of the patient;

expiratory gas receiving means for receiving expiratory gas from the patient during an expiration cycle of the patient, said expiration cycle including an end tidal air portion during which said expiratory gas includes end tidal air, said expiratory gas receiving means including means positioned in said photography area of said gantry means for selectively receiving said end tidal air;

control means coupled to said gantry means and to said expiratory gas receiving means for causing said scanning means to scan said portion of the patient and said end tidal air receiving means during said end tidal air portion of said expiration cycle to produce corresponding tomographic image data; and means for calculating the concentration of said tracer gas in the cerebal blood of the patient from said tomographic image data.

2. An apparatus according to claim 1, wherein:

said expiratory gas receiving means includes first conduit means for channeling a portion of said expiratory gas other than said end tidal air;

said end tidal air receiving means includes second conduit means for channeling said end tidal air, said scanning means producing said tomographic image data to correspond to said second conduit means separate from said first conduit means; and valve means coupled to said first and said second conduit means for selected directing said expiratory gas to said first and said second conduit means.

3. An apparatus according to claim 2, wherein said expiratory gas receiving means includes:

sensor means coupled to said valve means for detecting said end tidal portion of said expiration cycle; and means for controlling said valve means in response to said sensor means.

4. An apparatus according to claim 3, wherein said valve control means operates said valve means to direct said expiratory gas to said second conduit means in response to detection by said sensor means of said end tidal air portion of said expiration cycle.

5. An apparatus according to claim 4, wherein said valve control means operates said valve means to direct said expiratory gas to said first conduit means upon lapsing of a predetermined period of time after the detection of said end tidal air portion by said sensor means.

6. An apparatus according to claim 1, wherein said end tidal air receiving means comprises a storage chamber, and means coupled to said storage chamber for selectively supplying said end tidal air to said storage chamber.

7. An apparatus according to claim 6, wherein said expiratory gas receiving means includes:

sensor means for detecting said end tidal air portion of said expiration cycle; and flow control means responsive to said sensor means for causing said end tidal air to enter said end tidal air storage chamber upon detection of said end tidal air portion.

8. An apparatus according to claim 1, wherein said inspiratory gas means includes a tracer gas container, an oxygen gas container, and means including a mixture gas container coupled to said tracer gas and said oxygen gas containers for mixing selected amounts of said tracer gas and oxygen to produce a mixture gas.

9. An apparatus according to claim 8, wherein said inspiratory gas means includes means coupled to said mixture gas container for measuring a concentration of said mixture gas, and means coupled to said concentration measuring means for regulating said selected amount of oxygen in response to said measurement of said mixture gas concentration.

* * * * *

UNITED STATES PATENT AND TRADEMARK OFFICE
CERTIFICATE OF CORRECTION

PATENT NO. : 4,793,358

DATED : December 27, 1988

INVENTOR(S) : Tokunori Kimura et al.

It is certified that error appears in the above-identified patent and that said Letters Patent is hereby corrected as shown below:

Claim 1, Column 6, Line 67 change "gentry" to --gantry--.

Claim 2, Column 7, Line 39 change "selected" to --selectively--.

Signed and Sealed this

Seventh Day of August, 1990

Attest:

HARRY F. MANBECK, JR.

*Attesting Officer*    *Commissioner of Patents and Trademarks*